United States Patent
Guhl et al.

(10) Patent No.: US 11,703,810 B2
(45) Date of Patent: Jul. 18, 2023

(54) CONNECTED, MECHANICAL WINDING WATCH

(71) Applicant: Sequent SA, Zug (CH)

(72) Inventors: Harry Guhl, Basel (CH); Adrian Buchmann, Henley-on-Thames (GB)

(73) Assignee: Sequent SA, La Chaux-de-Fonds (CH)

( * ) Notice: Subject to any disclaimer, the term of this patent is extended or adjusted under 35 U.S.C. 154(b) by 961 days.

(21) Appl. No.: 16/510,425

(22) Filed: Jul. 12, 2019

(65) Prior Publication Data

US 2020/0026244 A1 Jan. 23, 2020

(30) Foreign Application Priority Data

Jul. 20, 2018 (CH) ..................... CH00895

(51) Int. Cl.
| | |
|---|---|
| *G04G 19/00* | (2006.01) |
| *H04W 4/38* | (2018.01) |
| *A61B 5/0205* | (2006.01) |
| *A61B 5/11* | (2006.01) |
| *A61B 5/00* | (2006.01) |
| *G04C 10/04* | (2006.01) |
| *G04G 9/00* | (2006.01) |

(Continued)

(52) U.S. Cl.
CPC ........... *G04G 19/00* (2013.01); *A61B 5/0205* (2013.01); *A61B 5/1112* (2013.01); *A61B 5/1118* (2013.01); *A61B 5/486* (2013.01); *A61B 5/681* (2013.01); *G04C 10/04* (2013.01); *G04G 9/007* (2013.01); *G04G 21/025* (2013.01); *G04G 21/04* (2013.01); *H04W 4/38* (2018.02); *A61B 5/024* (2013.01); *A61B 2562/0219* (2013.01); *H02K 35/00* (2013.01)

(58) Field of Classification Search
CPC ...... G04G 19/00; G04G 9/007; G04G 21/025; G04G 21/04; H04W 4/38; A61B 5/0205; A61B 5/024; A61B 5/1112; A61B 5/1118; A61B 5/486; A61B 5/681; A61B 2562/0219; G04C 10/04; H02K 35/00
See application file for complete search history.

(56) References Cited

U.S. PATENT DOCUMENTS 10,610,111 B1 * 4/2020 Tran ..................... A61B 5/411
2007/0223318 A1 9/2007 Nobs
(Continued)

FOREIGN PATENT DOCUMENTS

| EP | 0295744 A1 | 12/1988 |
|---|---|---|
| EP | 0547083-81 | 10/1994 |

(Continued)

OTHER PUBLICATIONS

Search Report for CH8952018, dated Nov. 13, 2018, 3 pages.

*Primary Examiner* — Orlando Bousono
(74) *Attorney, Agent, or Firm* — Blank Rome LLP

(57) ABSTRACT

An electronic watch having a timekeeper logic unit set to control a display of the time. A controller is in communication with an external device or with internet through a wireless interface of the watch. A mechanical energy harvester system is set to transform mechanical energy deriving from the movements of a wearer to electrical energy. A power manager circuit stores the electrical energy in a battery and/or in a capacitor, and to supply the logic unit, the controller and the wireless interface with energy stored in the battery and/or in the capacitor.

16 Claims, 2 Drawing Sheets

(51) Int. Cl.
*G04G 21/02* (2010.01)
*G04G 21/04* (2013.01)
*A61B 5/024* (2006.01)
*H02K 35/00* (2006.01)

(56) References Cited

U.S. PATENT DOCUMENTS

| | | | |
|---|---|---|---|
| 2013/0303087 A1* | 11/2013 | Hauser | H04W 4/80 455/41.2 |
| 2016/0028264 A1* | 1/2016 | Bernhard | G04C 10/00 307/21 |
| 2016/0150362 A1* | 5/2016 | Shaprio | G08B 21/0453 340/539.13 |
| 2016/0226542 A1* | 8/2016 | Tran | A61B 5/369 |
| 2016/0252883 A1 | 9/2016 | Inoue | |
| 2018/0004169 A1 | 1/2018 | Matsuzaki et al. | |
| 2018/0035793 A1* | 2/2018 | Davis | A45F 5/02 |
| 2018/0074462 A1* | 3/2018 | Helder | G06F 3/04883 |
| 2018/0078181 A1* | 3/2018 | Cronin | G16Z 99/00 |
| 2018/0126053 A1* | 5/2018 | Zilbershlag | A61M 60/50 |
| 2018/0184907 A1* | 7/2018 | Tran | G16Z 99/00 |
| 2019/0138068 A1* | 5/2019 | Park | G06F 1/26 |

FOREIGN PATENT DOCUMENTS

| | | | |
|---|---|---|---|
| EP | 1239349 | A1 | 9/2002 |
| EP | 1821163 | A2 | 8/2007 |
| EP | 3190469 | A1 | 7/2017 |

\* cited by examiner

CONNECTED, MECHANICAL WINDING WATCH

REFERENCE DATA

The present application claims priority of Swiss Patent Application 00895/18 of Jul. 20, 2018, in the name of Sequent SA, the contents whereof are hereby incorporated.

TECHNICAL FIELD

The invention relates to an electronic watch comprising sensors and a communication interface connectable to an information technology network, capable of displaying indications determined on the database coming from the network or from the sensors.

RELATED ART

Electronic mobile devices are commonly used and widely known. Devices such as laptops, tablets, mobile telephones, games consoles and music players are used in all the sectors of the industry and the entertainment sector and offer an infinity of services integrating information coming from a network interface to internet, from specific sensors, and from instruments for computing and elaborating information technology data.

Miniaturization efforts have enabled the creation of ever smaller and more practical mobile devices, and many examples are already known of "connected" or "smart" wrist watches capable of exchanging elements of information on Internet and displaying for example notifications to the wearer based on this information. Several wireless data exchange interfaces are used for this purpose, comprising, among others, cellular telephone networks, for example according to GSM, GPRS, UMTS, or any other suitable standard, and local wireless networks (WiFi, Bluetooth®, etc.).

Also known are wrist watches or devices, connected to a network or independent, equipped with all kinds of sensors, for example, GPS sensors, accelerometers etc., and processing modules set to provide indications of physical, sporting activity or state of health, integrating information coming from these sensors. These connected watches can use any suitable wireless communication system. However, they are more often based on a ow consumption local network, typically Bluetooth® LE, to be connected to a smartphone or to another device acting as a gateway.

Despite all the efforts implemented to limit the consumption of connected watches, battery capacity remains a factor limiting their use. Autonomy between two battery charges is often limited to a few days, or a few hours when the GPS or other functions are in high demand.

For example, through EP0295744, EP0547083, EP1239349, EP1821163 and other publications, electronic watches are also known that derive the energy necessary to their functioning from an electricity generator driven by the movements of the wearer.

BRIEF SUMMARY OF THE INVENTION

An aim of the present invention is to propose a connected watch whose use is not as limited by battery capacity as in the known devices.

According to the invention, these aims are achieved in particular by means of the object of the independent claim, preferred embodiment variants being covered by the dependent claims.

BRIEF DESCRIPTION OF THE FIGURES

Examples of implementation of the invention are indicated in the description illustrated by the attached figures, in which.

DETAILED DESCRIPTION

Figure 1:
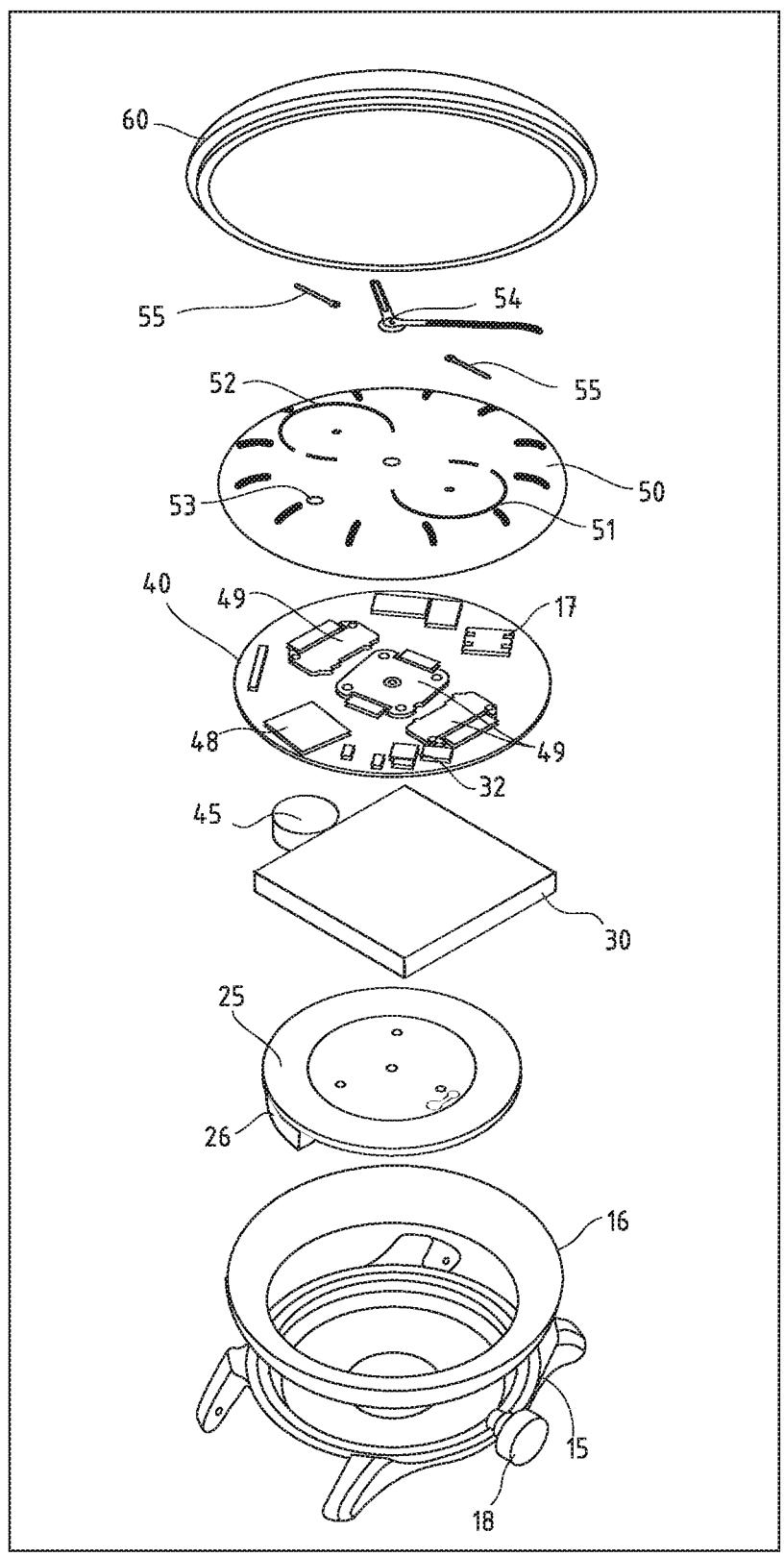
FIG. 1 illustrates the possible structure of a watch according to the invention.

Referring to FIG. 1, a possible embodiment of the invention consists in a wristwatch comprising an analog face 50 with two hands 54 in the center, as well as two small analog indicators, for example an indicator 51 at three o'clock and an indicator 52 at nine o'clock, with two small hands 55.

The main function of the hands 54 in the center is that, conventional, of indicating what time it is. The use of hands in the center for other indications can also be envisaged within the context of the invention.

The small indicators 51, 52 can be used for any function. In a preferred variant an indicator, for example the indicator 52 is used to indicate at any time the available energy reserve, which is linked, as will be better seen later, with the state of charge of the watch battery while the other indicator, for example the indicator 51, can be used to indicate any kind of information. One of the small indicators preferably displays a "biofeedback" corresponding to a physical activity accumulated in a determined time interval relative to a given target.

So as to define the ideas, the indicator 51 can be programmed to indicate a physical activity determined by one or more movement and/or physical activity sensors 17, The invention can include any kind of sensor comprising for example a step counter, an accelerometer, a GPS receiver or a heart rate monitor. The sensors 17 are preferably included in the watch itself, but the invention also relates to variants in which the movement sensors are integrated in an external device with which the watch communicates, for example a mobile telephone or a chest belt.

The face preferably also comprises one or more LED 53 diodes or elements usable for displaying a visual alert. These elements can be activated to notify predetermined situations to the user, such as for example the arrival of a message or a pre-registered appointment. The visual alert can also include a sound signal and/or a vibration through the vibrator 45.

The watch of the invention preferably also includes an electronic module 40, in the shape of a printed circuit for example, preferably comprising the sensors 17 mentioned above, step motors 49 for activating the hands 54, 55, and one or more logic circuits for controlling the watch and performing its different functions.

The electrical energy necessary to the functioning of the watch is provided by an energy harvester unit 25. In a preferred variant, the energy harvester unit 25 includes an eccentric oscillating weight 26 moved by the movements of the wearer of the watch, like the oscillating weight of an automatic clock movement, and an electricity generator 27

(schematically illustrated on FIG. 2) for transforming these movements into electrical energy.

The generator module preferably comprises a spring, tensioned by the movement of the oscillating weight and an automatic clutch device for activating the generator when the spring tension exceeds a predetermined threshold. Once the spring is relaxed, the generator stops and this cycle, which can be repeated several times a minute if the wearer is very active, starts again.

This variant is advantageous because it enables the generator to be turned very fast, thus reducing part of the energy loss that takes place if it turns too slowly. It is possible nevertheless to drive the generator directly through the oscillating weight, with a transmission synchronous with an appropriate reduction ratio, still engaged. Suitable energy recovery devices are produced by Kinetron (Tilburg, The Netherlands), among others.

The invention also approves variants with manual rewinding in which the energy harvester unit can be driven by a crown of the watch, or by another element of the watch on which the user can act, a bezel for example. The ability to drive the energy harvester unit 25 manually does not exclude the presence, in the same watch, of an oscillating weight for performing the same function automatically.

Figure 2:
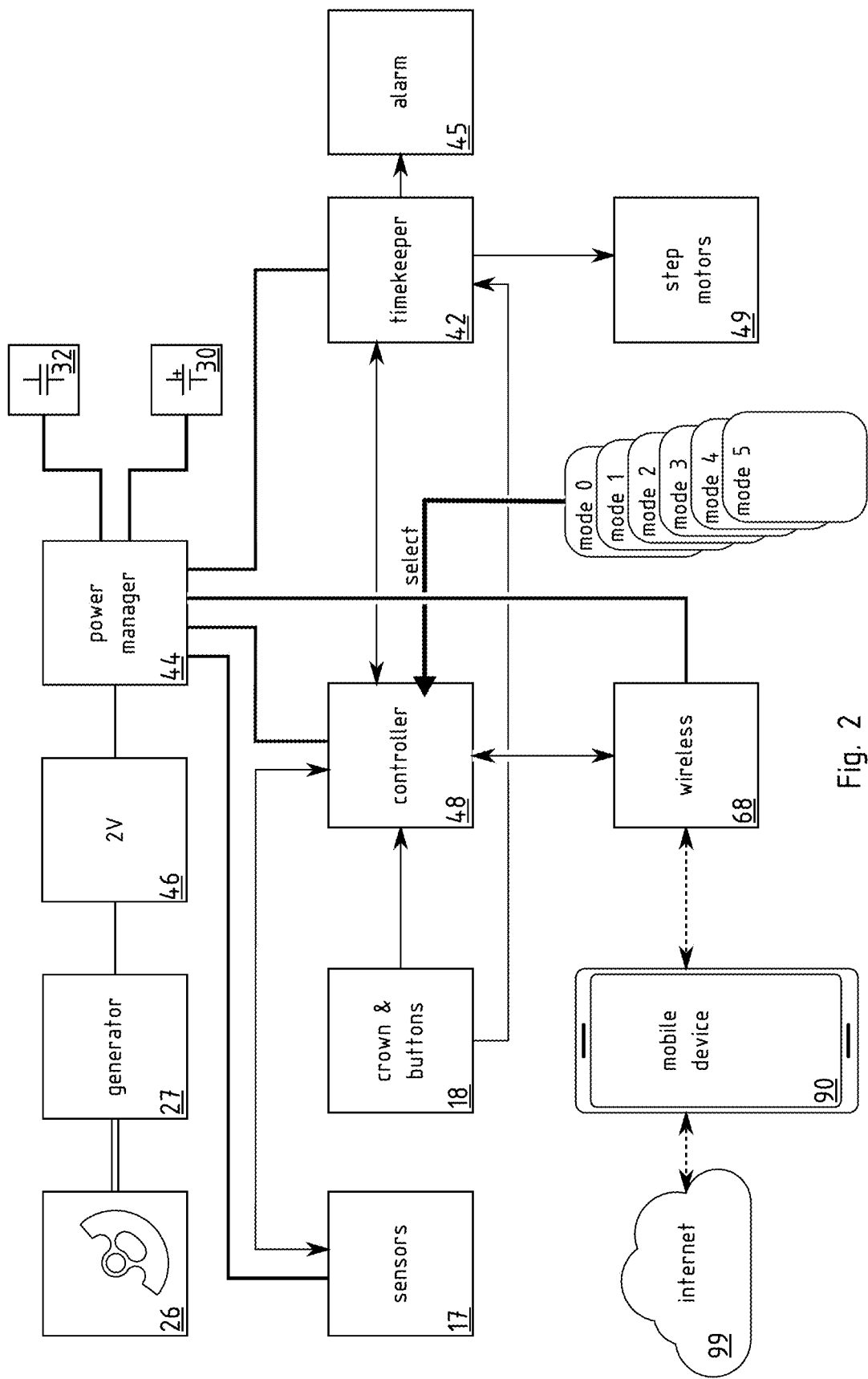
FIG. 2 illustrates, through a block diagram, the possible functional elements of a watch according to the invention and their interactions

FIG. 2 schematically illustrates the elements involved in the functioning of a watch according to the invention. This illustration is proposed solely in a descriptive aim and it should not be understood that all the drawn elements are essential, or that they must be physically embodied as distinct elements. As it is a question of functioning blocks, several functions can be ensured by a single multifunctional device, or by software elements as the case may be.

Importantly, the watch includes a power manager circuit 44 whose function is to transform, for example, the alternating current produced by the generator into direct current suitable for charging accumulators, and to store this energy. In many cases, the production of electrical energy by the generator 27 is discontinuous; the power manager 44 advantageously uses one or more capacitors or ultra-capacitors 32 to handle production peaks as well as a rechargeable battery 30, for example a Li-ion, Li-poly or NiMH accumulator.

Another function of the charger is that of supplying a stable power supply for the other electronic components of the watch. Advantageously, the charger circuit includes a voltage multiplier 46 for raising the voltage level present at the output of the generator 27. Several circuits can be used for this purpose, for example doublers with diodes or charge pumps.

Importantly, the watch of the invention includes two logic units that can be activated selectively, depending on the immediate availability of energy. A first logic unit 42 has a timekeeping function and can be an electronic quartz watch movement. The timekeeper 42 controls among others the step motors 49 that activate the hands 54, 55. This component of the watch is embodied with ultra—low consumption integrated circuits specially designed for watchmaking applications.

A second logic unit 48 oversees the "smart" functions of the watch. This unit could be embodied by an ultra-low consumption microcontroller, or by any other suitable component. The computing performance and resources of this second logic unit are clearly superior to those of the first timekeeper unit 42 and its energy consumption is naturally greater. The second logic unit is preferably in charge of managing the sensors 17 and the wireless communication interface 68, and is active, and activates the peripherals it manages according to a defined program and the immediate availability of energy.

The wireless communication interface 68 enables the watch of the invention to be linked to any service or source of data available on internet. Although a direct connection could be envisaged, a local low consumption network interface like Bluetooth® LE for example is preferable for energy reasons. A telephone or another mobile device 90 endowed with an internet connection is then used as a communication intermediary. The telephone 90 is also used, through a specific application, to control the functions of the watch and to choose the information to display.

The watch of the invention preferably has several functioning modes that differ for the number of activated functions, the wealth of the displayed information and by their energy consumption.

The basic function of the watch, that of displaying what time it is, is entrusted entirely to the first timekeeper logic circuit 42 and does not require any activation of the second logic circuit 48, the sensors 17 or the wireless interface 68. The watch of the invention thus includes a minimum consumption functioning mode; the "time" mode, in which the time is displayed by the hands 54, is active, and the "smart" functions are inactive. The rechargeable battery 30 is preferably dimensioned so that the autonomy of the watch in this state is several days, preferably longer than 100 days. This autonomy corresponds to the maximum time during which, starting from a full state of charge of the battery, the watch can keep time without being worn.

When the watch is worn, the energy produced by the generator 27 allows the battery to be recharged and additional functions linked with the sensors 17 and/or information from the internet to be activated through the wireless interface 68. These functions can include, for example:

a. monitoring of the level of physical activity and/or the asleep/awake state by one or more sensors, for example an accelerometer, a vibration sensor or a movement sensor;

b. heart monitoring by an optical or electric sensor;

c. tracking of geographical position through a GPS/Galileo or any other positioning system;

d. display of notifications triggered by Internet events, for example e-mails, text messages or appointments.

These functions can be combined in several functioning modes, for example:

1. the "time" mode with aforementioned maximum autonomy;

2. "activity" mode in which the watch determines and periodically saves, with a predetermined frequency, the level of physical activity, and/or the state of wakefulness;

3. a first "sport" mode in which the watch, in addition to physical activity, determines and also saves the heart rate, for example once each minute;

4. a second "sport" mode with monitoring and simultaneous recording of the activity and geographical position;

5. a third "sport" mode combining the sport modes I and II;

6. a "connected" mode with monitoring of physical activity and display of notifications;

7. In the "connected" mode, the watch can also receive and transmit through the wireless interface 68 all kinds of data that do not result in a notification, but are useful to the functioning of the watch and/or to the implementation of "smart" functions. For example, the watch can receive updates of its embedded software, synchronize on time servers to set the time and/or to adjust its operation, download geopositioning assistance data (GPS assistance) and so on.

The functioning modes 1-6 can be selected through a deliberate action of the user, for example pressure on the crown 18 or on a push button (not illustrated) or through an app executed on the mobile device 90.

The watch of the invention is preferably programmed to change automatically to a least consumption functioning mode according to the state of charge of the battery 30 and the capacitors 32, and the electric power supplied by the generator 27. This way, if the energy generated by the wearer is insufficient to maintain an activated mode indefinitely, the watch changes automatically to a least consumption mode, for example the "time" mode, so that the time display is maintained.

In a variant, the least consumption functioning mode provides that the analog display of the time—for example the two hands 54 in the center that indicate the hours and the minutes—is stopped when the watch is immobile for a more or less prolonged period and starts again when the watch is moving. When the display is restored, the hour and minute hands move rapidly ("trot") until the position corresponding to what time it is reached, as it has been maintained by the timekeeper logic circuit 42.

As was seen above, the small hand at nine o'clock is preferably used to display the state of charge of the battery 30, while the other gives a "biofeedback" indication corresponding to a physical activity accumulated in a determined time interval, relative to a given target. This function can include the following steps for example:

a. The user defines, through an app executed on the mobile device 90, a physical activity objective and an interval of time during which the activity should be completed: for example 10,000 steps in 24 hours.

b. The mobile device 90 transfers these instructions to the controller 48 of the watch through the Bluetooth® interface 68.

c. The controller 48 activates a functioning mode in which the step counting function is active, for example, the above "activity" mode. The steps of the user are counted and accumulated in a variable.

d. The controller 48 periodically calculates the percentage of activity relative to the target to be attained and controls (potentially through the intermediary action of the timekeeper 42) the movement of the small hand to three o'clock as a consequence. For example, the hand will move to the middle of its travel when the wearer has accumulated 5000 steps, and will reach its upper limit if and when the wearer has accumulated 10,000 steps.

e. At the end of a 24 hour period, the accumulator variable is reset to zero and the hand moved to the start of the scale. The cycle is repeated every 24 hours.

REFERENCE NUMBERS USED ON THE FIGURES

15 back cover
16 caseband
17 movement and/or physical activity sensors
18 crown
25 energy harvester
26 energy source
27 generator
30 battery
32 capacitors
40 printed circuit
42 timekeeper logic unit
44 power manager
45 vibrator
46 voltage multiplier
48 controller
49 step motors
50 face
51 function indicator
52 energy reserve indicator
53 visual alert
54 center hands
55 small hand
60 glass
68 wireless interface
90 mobile telephone
99 Internet

The invention claimed is:

1. A wristwatch, comprising a mechanical energy harvester device, set to transform mechanical energy deriving from movements of a wearer of the wristwatch to electrical energy, a controller in communication with an external device or with internet through a wireless interface of the wristwatch, said controller being programmed to have several predefined functioning modes having different energy consumptions, and to select automatically a lower consumption functioning mode according to a state of charge of a battery and/or capacitors of the wristwatch, and the electric power supplied by the mechanical energy harvester device.

2. The wristwatch of claim 1, further comprising a logic unit set to control a display of the time, a power manager for storing the electrical energy in the battery and/or in the capacitors, and to supply the logic unit, the controller and the wireless interface with energy stored in the battery and/or in the capacitors.

3. The wristwatch of claim 2, further comprising one or more sensors supplied in energy by the power manager, the one or more sensors comprising one or more among: physical activity sensor, accelerometer, receiver for satellite geopositioning, heart rate monitor.

4. The wristwatch of claim 1, in which the mechanical energy harvester device includes an oscillating weight and/or a crown, and/or a bezel, driving a generator.

5. The wristwatch of claim 1, further comprising a display component, controllable by the controller, for providing a biofeedback indication corresponding to a physical activity accumulated in a determined time interval.

6. The wristwatch of claim 1, further comprising a display component, controllable by the controller, for providing an energy reserve indication.

7. The wristwatch of claim 1, further comprising a display component, controllable by the controller, for providing the wearer with a notification triggered by internet events.

8. The wristwatch of claim 1, further comprising an analog time display.

9. The wristwatch of claim 1, said controller having a low consumption functioning mode with timekeeping function in which the logic unit is active, while the controller, the one or more sensors and the wireless interface are deactivated.

10. The wristwatch of claim 9, wherein an analog display of the time is stopped when the wristwatch is immobile and in the low consumption functioning mode and started again when the watch is moving.

11. The wristwatch of claim 10, wherein the battery and/or the capacitors are dimensioned to ensure an autonomy longer than 100 days in the low consumption mode, the autonomy corresponding to the maximum time during which, starting from a full state of charge of the battery and/or the capacitors, the wristwatch can keep time without being worn.

12. The wristwatch of claim 3, the wristwatch being set to transmit information obtained from the one or more sensors to an electronic device connectable to the wireless interface of the wristwatch; the information received by the one or more sensors comprises, among others, one or more among: physical activity of the wearer of the wristwatch, geographical position, heart rate or vascular rhythm.

13. The wristwatch of claim 12, further comprising a display device connectable to the wireless interface of the wristwatch, the display device being programmed to display the information obtained.

14. The wristwatch of claim 13, wherein the display device comprises a telephone.

15. The wristwatch of claim 13, the display device being configured to display the information obtained in the form of an activity indicator, or a biofeedback indication corresponding to a physical activity accumulated in a determined time interval.

16. A wristwatch, comprising a mechanical energy harvester device, set to transform mechanical energy deriving from movements of a wearer of the wristwatch to electrical energy, a controller in communication with an external device or with internet through a wireless interface of the wristwatch, said controller being programmed to have several predefined functioning modes, that differ for a number of activated functions, a wealth of displayed information and by their energy consumption, and to select automatically a lower consumption functioning mode according to a state of charge of a battery and/or capacitors of the wristwatch, and the electric power supplied by the energy harvester device.

* * * * *